(12) United States Patent
Hauger et al.

(10) Patent No.: US 10,078,205 B2
(45) Date of Patent: Sep. 18, 2018

(54) OPTICAL OBSERVATION DEVICE FOR OBSERVING AN EYE

(75) Inventors: Christoph Hauger, Aalen (DE); Fenny Nauli, Aalen (DE); Fritz Straehle, Heubach (DE); Martin Fanenbruck, Oberkochen (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 12/928,821

(22) Filed: Dec. 20, 2010

(65) Prior Publication Data

US 2011/0205489 A1    Aug. 25, 2011

Related U.S. Application Data

(60) Provisional application No. 61/284,538, filed on Dec. 18, 2009.

(30) Foreign Application Priority Data

Dec. 18, 2009    (DE) .................. 10 2009 058 792

(51) Int. Cl.
```
A61B 3/14       (2006.01)
A61B 3/00       (2006.01)
G02B 21/22      (2006.01)
A61B 3/13       (2006.01)
A61B 90/20      (2016.01)
```

(52) U.S. Cl.
CPC .............. *G02B 21/22* (2013.01); *A61B 3/132* (2013.01); *A61B 3/0008* (2013.01); *A61B 90/20* (2016.02)

(58) Field of Classification Search
USPC ........ 351/200, 206, 203, 216, 222, 221, 233
See application file for complete search history.

(56) References Cited

U.S. PATENT DOCUMENTS

| | | | |
|---|---|---|---|
| 5,993,001 A * | 11/1999 | Bursell et al. ................. | 351/212 |
| 6,347,244 B1 * | 2/2002 | Dubnack ....................... | 600/476 |
| 7,387,385 B2 * | 6/2008 | Sander ............... | G02B 21/0012 |
| | | | 351/206 |

(Continued)

FOREIGN PATENT DOCUMENTS

| CN | 1792318 A | 6/2006 |
|---|---|---|
| CN | 201072076 Y | 6/2008 |

(Continued)

*Primary Examiner* — Brandi Thomas
(74) *Attorney, Agent, or Firm* — Kriegsman & Kriegsman

(57) ABSTRACT

An optical observation device (100) for observing an eye (22) is described, having a microscope means (1), in particular a stereoscopic means, for observation of the anterior segment of eye (22), and having a means (2) for visualizing the retina of eye (22), particularly a stereoscopic means, with at least one camera (21), in particular, a digital camera. In order to provide an optical observation device (100), with which the anterior eye (22) and the retina can be observed alternately, in particular stereoscopically, in a constructively simple way, it is provided according to the invention that visualizing means (2) is designed as an attachment module in front of microscope means (1) and that visualizing means (2) is disposed on a positioning device (12) and can be positioned in front of eye (22), in particular, at a short distance in front of eye (22), via positioning device (12).

12 Claims, 1 Drawing Sheet

(56) References Cited

U.S. PATENT DOCUMENTS

| | | | |
|---|---|---|---|
| 8,556,427 B2* | 10/2013 | Zund | 351/221 |
| 2003/0227673 A1* | 12/2003 | Nakagawa | 359/380 |
| 2005/0232916 A1* | 10/2005 | Martin | A61K 31/192 424/130.1 |
| 2007/0019160 A1* | 1/2007 | Kleen et al. | 351/206 |
| 2007/0189755 A1* | 8/2007 | Gutridge et al. | 396/182 |

FOREIGN PATENT DOCUMENTS

| | | |
|---|---|---|
| CN | 101316547 A | 12/2008 |
| DE | 35 39 009 A1 | 5/1987 |
| DE | 94 15 219 U1 | 11/1994 |
| DE | 41 14 646 C2 | 2/1996 |
| DE | 101 40 402 A1 | 4/2002 |
| DE | 103 02 401 A1 | 7/2004 |
| DE | 10 2005 032 501 A1 | 3/2006 |
| DE | 10 2007 042 571 A1 | 4/2008 |
| EP | 1 889 567 A2 | 2/2008 |

\* cited by examiner

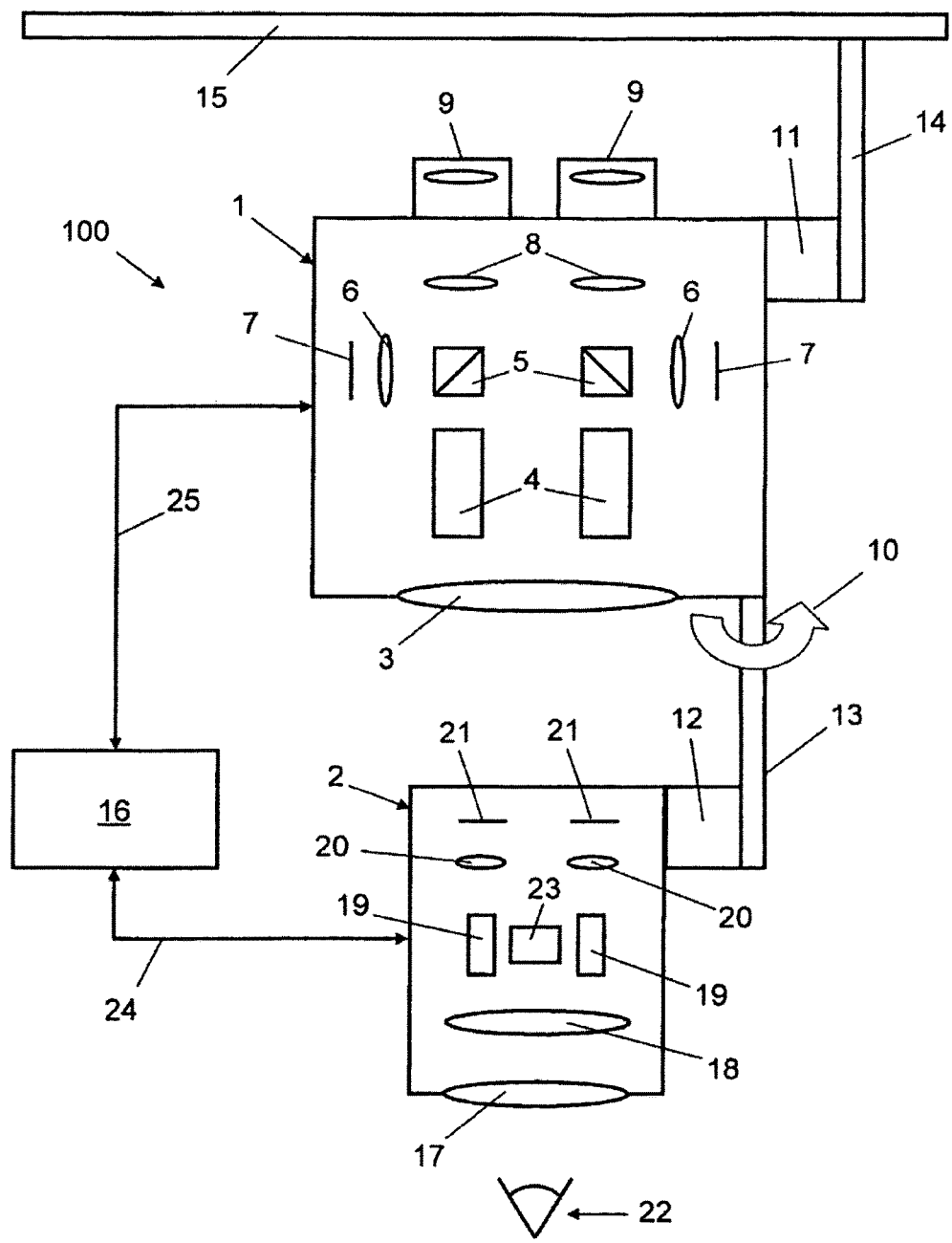

OPTICAL OBSERVATION DEVICE FOR OBSERVING AN EYE

CROSS-REFERENCE TO RELATED APPLICATIONS

The present application claims the benefit under 35 U.S.C. 119(e) of U.S. Provisional Patent Application No. 61/284,538, filed Dec. 18, 2009, the disclosure of which is incorporated herein by reference.

BACKGROUND OF THE INVENTION

The present invention relates to an optical observation device for observing an eye according to the preamble of patent claim 1. In particular, the present invention relates to an optical observation device, by means of which the anterior eye and the retina can be alternately observed, in particular, stereoscopically.

For this purpose, different solutions are already known in the prior art. For example, an alternating observation can be achieved by means of a stereoscopic operating microscope with a fundus imaging system, as is described, for example, in the German Utility Model G 94 15 219.5 U1. The known fundus imaging system comprises an ophthalmoscopic loupe and a reducing lens, which are positioned underneath the principal objective of the operating microscope, in order to make possible an imaging of the fundus, and thus the retina of the eye. An intermediate image of the retina is produced by means of the ophthalmoscopic loupe and this image is observed with the operating microscope. The reducing lens shortens the working distance and thus makes possible the imaging of the intermediate image in the intermediate image plane in front of the eyepiece of the operating microscope. With the help of a positioning device, the ophthalmoscopic loupe can be positioned in such a way that the fundus of the eye is sharply imaged.

This image, which is observed in this way, however, is vertically and laterally reversed as well as pseudo-stereoscopic, i.e., front and back are reversed in depth perception. For this reason, a correcting of the image and a pupil reversal are necessary, in the known solution, in order to be able to operate microsurgically.

Different fundus imaging systems for operating microscopes with image correction and pupil reversal are described in the publications DE 101 40 402 A1, DE 41 14 646 C2, or DE 35 39 009 A1.

In ophthalmic surgery, operating microscopes are frequently used for interventions in the anterior eye and for interventions on the retina. The cataract operation is a frequent intervention in the anterior eye, whereas so-called epiretinal membrane peeling represents a typical intervention on the retina.

Direct contact glasses, which are placed on the cornea of the eye, are also used very often in ophthalmic surgery as an alternative to ophthalmoscopic loupe/reducing lens systems. In the case of direct contact glasses, an intermediate image of the retina is not produced in the imaging beam path of the operating microscope, but rather the fundus is imaged directly with the operating microscope. In this case, an image correction and a pupil reversal are not necessary.

The older publication EP 1 889 567 A2 describes an operating microscope with a fundus imaging system in which the illumination is guided past the ophthalmoscopic loupe in order to avoid disruptive reflections.

An operating microscope is described in DE 103 02 401 A1, which is constructed similarly to the one in the above-named G 94 15 219 U1. The operating microscope has a microscope means. In addition, a means for visualizing is provided, which serves for diagnosing the retina. The visualizing means provides a camera for recording images of the retina. In addition, the operating microscope provides an attachment means with attachment lenses, which—with the above-described disadvantages—can be introduced into the optical beam path of the microscope means. The difference relative to G 94 15 219 U1 consists only in that the image of the retina is no longer presented in the optical beam path; rather, the image in the operating microscope is decoupled via a beam splitter and is introduced into a camera.

In the case of solutions known in the prior art, an alternating between the anterior and posterior regions of the eye is produced either by swinging in an ophthalmoscopic loupe/reducing lens combination or by placing a direct contact glass on the cornea and appropriate focusing of the operating microscope.

The named prior art, however, has a number of disadvantages, for example, an image correction and a pupil reversal are necessary when an ophthalmoscopic loupe and reducing lens are used. The image correction and pupil reversal can be accomplished in known systems only with a great deal of complexity, such as is clarified in the publications DE 101 40 402 A1, DE 41 14 646 C2 or DE 35 39 009 A1.

In addition, only a moderate imaging quality is achieved when an ophthalmoscopic loupe is used. The reason for this is that the ophthalmoscopic loupe must be autoclavable and for this reason comprises a single lens—and often, in fact, this does not have an antireflection coating.

Also, an ophthalmoscopic loupe can be positioned only with a great deal of effort and imprecisely for the surgeon, since it is joined only very loosely with the operating microscope for safety reasons and thus can be very easily displaced laterally off-center. Another difficulty with the positioning consists of the fact that the distance of the ophthalmoscopic loupe from the eye is not defined and vignetting can occur at too great a distance.

Reducing lenses, ophthalmoscopic loupes and their mounts usually need to be autoclavable. This requirement for sterilization is complicated and makes progress difficult for the surgical operation.

The conventional illumination of an operating microscope for ophthalmic surgery is designed either as oblique lighting or as coaxial lighting with oblique lighting. When an ophthalmoscopic loupe is used, in all cases, there are reflections of the illumination at the interfaces of the ophthalmoscopic loupe.

SUMMARY OF THE INVENTION

The object of the present invention is thus to further develop an optical observation device of the above-named type in such a way that the described disadvantages can be circumvented. In particular, an optical observation device will be provided, by means of which the anterior eye and the retina can be observed alternately, particularly stereoscopically, in a constructively simple way.

This object is achieved according to the invention by the optical observation device having the features according to the independent patent claim 1. Further features and details of the invention can be taken from the subclaims, the description and the drawings.

According to the invention, an optical observation device for observing an eye is provided, having a microscope means for observation of the anterior segment of the eye, and having a means for visualizing the retina of the eye, with at least one camera, in particular, a digital camera. The optical observation device is hereby characterized according to the invention in that the visualizing means is designed as an attachment module in front of the microscope means and that the visualizing means is disposed on a positioning device and can be positioned in front of the eye, in particular, at a short distance in front of the eye, via the positioning device.

Advantageously, the microscope means and/or the means for visualizing the retina of the eye can be designed stereoscopically and can thus form a stereoscopic optical observation device.

The present invention, in particular, is characterized by a visualizing means, which is designed in a particular manner for visualizing the retina of the eye to be observed.

The visualizing means makes possible the alternate imaging, particularly stereoscopic imaging, of the anterior eye and the retina. The basic concept includes the use of a conventional microscope means, for example, a conventional operating microscope, for the anterior eye segment. Here, a visualizing means is used instead of the ophthalmoscopic loupe/reducing lens combination. The entire optical observation device can thus be used in the two working modes of "anterior eye" and "retina".

The optical observation device according to the invention thus makes possible, in particular, an intraoperative visualization of the retina and replaces the ophthalmoscopic loupe/reducing lens combination or substitutes for a direct contact glass that is used in combination with an operating microscope.

The preferred field of application for the observation device according to the invention is, for example, ophthalmic surgery, but the invention is not limited to this field of application.

An optical observation device for observing an eye, which has a number of subassemblies designed in a particular manner, is provided according to the invention.

First, the optical observation device has a microscope means, particularly a stereoscopic microscope means, for observing the anterior segment of the eye. Here, for example, this may involve an operating microscope means, which can be used, in particular, in the field of ophthalmic surgery. In this case, the invention is not limited to specific embodiments of the microscope means. Microscope means of the named type are already known in the prior art and are familiar to the person skilled in the art.

In addition to the components that are familiar in such microscope means, such as objective, eyepiece, optionally tube optics or the like, the microscope means, for example, an operating microscope means for ophthalmic surgery can have an imaging beam path, in particular, a stereoscopic imaging beam path. Magnifications typically up to 20× and/or at least one illumination beam path, for example, in the form of an oblique illumination, a 0° illumination, a stereo/coaxial illumination, or the like, which is adapted to the specific application, can be advantageously provided.

In ophthalmic surgery, illumination and observation beam paths can be designed for a working distance—for example a fixed distance—in the range of 175 mm to 300 mm. This large working distance offers two advantages, in particular: On the one hand, a sufficiently dimensioned free space is formed in the region of the surgical field for the hands of the surgeon and the instruments; on the other hand, it makes possible an ergonomic operation, since the eyepiece of the operating microscope is found at a height corresponding to an upright seated position.

For example, the microscope means can be formed or designed as a visual microscope means. In another embodiment, it can be advantageously provided that the microscope means can be formed or designed as a digital microscope means.

If a digital microscope means is used, in particular, the known 3D representation possibilities are used, such as, for example, a monitor, BOOM, HMD. A BOOM involves, in particular, a digital viewing with an eyepiece that is attached particularly on a support arm. A control device, which may advantageously involve the control device that is described in greater detail below, can present the respective image data, for example, automatically, when the microscope means and the visualizing means are used in combination, for example, stereoscopically, and even simultaneously.

A positioning device can be provided advantageously for the microscope means. This device can advantageously make possible a number of degrees of freedom.

For example, it may be provided that three and up to six maximum degrees of freedom can be provided, for example, x, y, z, r, theta, phi.

In addition, the optical observation device has a means, in particular, a stereoscopic means, for visualizing the retina of the eye. Also, in this respect, the invention is not limited to specific embodiments. For example, the visualizing means may involve a digital microscope, particularly a digital retina microscope. The visualizing means provides at least one camera, particularly a digital camera, by means of which images of the retina can be recorded. Additionally, the visualizing means may have additional optical elements, as will be explained in more detail below, in the further course of the description. An advantageous embodiment of the visualizing means provides at least one retina camera, particularly a digital camera, at least one other optical apparatus, as well as a means for transmitting data to a receiving means, for example, a reading device. The receiving means can be, for example, a component of the microscope means and/or a component of a control device, which will be explained in more detail below in the further course of the description.

The visualizing means is configured in a special way according to the invention. According to the invention, the visualizing means is designed as an attachment module in front of the microscope means. In addition, the visualizing means is disposed on a positioning device. The visualizing means can be positioned in front of the eye, in particular, at a short distance in front of the eye, by means of the positioning device. Advantageous, but non-exclusive examples will be described below in greater detail for this purpose.

The positioning device can advantageously make possible a number of degrees of freedom. For example, it may be provided that three and up to six maximum degrees of freedom can be provided with the positioning device, for example, x, y, z, r, theta, phi.

In the "retina" working mode, the microscope means can take over, for example, the function of a surrounding field observation: Thus, for example, what is found in the surrounding region of the eye can be monitored and displayed, for example, the orientation of instruments.

The transmission of data from the visualizing means can be provided advantageously to the microscope means and/or to a control device. For example, it can be provided that the data can be transmitted via cable. The image, video, and other data can be transmitted from the visualizing means, however, also in other ways, for example, also via wireless or via a modulation of the illumination light of the visualizing means. In this case, the visualizing means and the microscope means and/or the control device advantageously provide interfaces designed to correspond to one another.

Instead of an ophthalmoscopic loupe and a reducing lens in combination with an operating microscope, now, according to the invention, a system for imaging the retina, in particular a digital system, especially a stereoscopic system, is used in combination with an operating microscope—either a visual or digital microscope. In this way, the visualizing means in the working mode advantageously is only a short distance from the eye to be observed.

Advantageously, the microscope means has at least one observation beam path. In this case, the visualizing means is disposed advantageously, for example, at the microscope means, by means of the positioning device, so that it can be swung in and out alternately into the observation beam path. For example, the visualizing means can be disposed on a suitable retaining device by means of the positioning device. For example, the retaining device can be disposed on the microscope means. For example, it may be provided for this purpose that the retaining device is disposed on the microscope means via a rotating joint or hinge for swinging the visualizing means in and out of the beam path of the microscope means. In another configuration, it may be provided that the positioning device is disposed on the retaining device via a rotating joint or hinge.

According to an advantageous embodiment, an optical observation device is provided, comprising a visual or digital microscope means, particularly a stereoscopic microscope means, for example, an operating microscope, for the anterior eye segment, a visualizing system for the retina that is particularly a digital system and especially a stereoscopic system—a so-called retina digiscope, whereby the visualizing means can be alternately swung in and out via a suitable retaining device, and thus images, particularly stereoscopic images, can be produced alternately between the anterior and posterior eye segments.

In another configuration, the visualizing means can have at least one first optical element for generating an intermediate image of the retina. This optical element can also be removed. In this case, advantageously, a direct contact glass and the rest of the optical elements of the visualizing means are used.

Preferably, in such a case, it may be further provided that the camera is disposed in the plane of the intermediate image, which is produced by the first optical element.

Advantageously, the visualizing means can have a means for producing a stereo image. Advantageously, this means is provided in the beam path in front of the camera. This means is advantageously designed in such a way that it produces two parts of the beam path that alternate sequentially over time, one after the other, so that a stereo image is produced. In this case, the invention is not limited to specific embodiments. For example, such a means may involve a shutter.

In another configuration, the visualizing means may advantageously have at least one other, second optical element. Here, this may involve, for example, an objective element and/or an optical magnification means.

The optical design of the visualizing means can thus vary advantageously. For example, in the case of a second optical element, which can be used advantageously for focusing, it may involve an element with a fixed focal length and/or a varioscope and/or a zoom system or a Galileo changing system or the like.

A variable magnification, which can be provided with the optical elements of the visualizing means, can be used advantageously for varying the object field on the retina. The use of different ophthalmoscopic loupes or contact glasses can thus be dispensed with. Also, the visualizing means can advantageously be designed in such a way that an automatic focusing of the imaging optics of the visualizing means is possible. In another configuration, the visualizing means is also advantageously formed in such a way that a tracking of the eye is possible, particularly in the three axes x, y and z.

In another configuration, a protective covering, particularly a covering that can be sterilized, can advantageously be provided for the visualizing means. It is preferred if the entire visualizing means is packed with a sterile protective covering, for example, a cloth drape, analogously to a conventional operating microscope. In such a case, it is then not necessary to use autoclavable elements.

Advantageously, the visualizing means may have an illumination device for illuminating the eye, particularly for illuminating the retina of the eye. In particular, a positioning of the visualizing means at a short distance from the eye leads to a compact optics for the observation beam path. For this reason, it is especially possible that the illumination of the retina is guided between the two observation beam paths, for which reason, reflections can be avoided.

In another configuration, it is advantageously provided that the optical observation device has a display for displaying images produced by the camera. Alternatively or additionally, it can advantageously be provided that the microscope means has at least one eyepiece and that the optical observation device has a means for reflecting the images produced by the camera into the eyepiece. The images recorded with the visualizing means are advantageously displayed on a suitable display, in particular, a stereoscopic display. If the microscope means is a visual system, the image data of the visualizing means, particularly stereoscopic image data, can be reflected advantageously by means of data reflection into the eyepiece of the microscope means.

Preferably, the optical observation device can have a control device, particularly for controlling the visualizing means and/or the positioning device of the visualizing means and/or of the microscope means. Advantageously, the control device can represent a type of monitoring or control device. It can advantageously be designed in order to transmit data, for example, image data or video data, between the visualizing means and the microscope means. It can also be designed in order to control the settings for the two working modes of "anterior eye" and "retina". In such a case, for example, the control device can be designed for activating the autofocus for the microscope means and/or the visualizing means and/or the positioning of the microscope means and/or of the visualizing means, and/or the turning on and off of the necessary/unnecessary illumination, as the case may be, of the microscope means and/or of the visualizing means, or the like. In particular, the control device is designed for data exchange—image data, video data, settings for "anterior eye" and "retina" working modes between microscope means and visualizing means.

Advantageously, the visualizing means can be designed as a type of intrinsic or unique, small microscope means, particularly a digital microscope means, with its own objective lens and optionally with a magnification means, for example, a zoom system.

In contrast to the solutions known from the prior art, in the case of the present invention, an optical element, for example, in the form of an ophthalmoscopic loupe and a camera, are introduced into the beam path in the simplest case by the visualizing means. The beam path to the camera then advantageously also no longer passes through the objective element of the microscope means. The camera can be advantageously disposed in the intermediate image, which is produced by the optical element. A system for image reversal and image correction is no longer necessary.

This can now be provided electronically, in particular.

Advantageously, the optical observation device can have a number of other components. These other components, for example, can be provided in the control device and/or the microscope means and/or the visualizing means.

Advantageously, a means for the automatic alignment of the visualizing means in the lateral direction—e.g., a centering, for example, on the pupil of the eye—and for controlling the positioning unit, on which the visualizing means is disposed, can be provided by evaluation of the camera signals.

Preferably, a means for the automatic focusing of the imaging optics of the visualizing means onto the fundus of the eye can be provided. For example, this focusing means can be provided by moving the entire visualizing means using the positioning device or by focusing with the help of optical components in the visualizing means.

In another configuration, a means for tracking the eye, at least in the three axes x, y and z can be provided. In particular, the means for the corresponding tracking can be designed with the help of the positioning device and/or for focusing with the help of the optical elements in the visualizing means.

Advantageously, the optical observation device can be designed in such a way that the swinging in and out of the visualizing means can be provided so that the position and thus the focus of the microscope means remains placed on the anterior eye. Thus both systems—microscope means and visualizing means—always remain focused on the respective objects, the anterior and posterior eye regions, when these systems are swung in and out.

Advantageously, the optical observation device is designed in such a way that an automatic positioning of the visualizing means in the x,y,z direction and/or a tracking function and/or an introduction of the image data, particularly stereoscopic image data, into the eyepiece of the microscope means can be provided.

BRIEF DESCRIPTION OF THE DRAWING

The invention will now be explained in more detail based on an embodiment example with reference to the attached drawing. The single FIGURE here shows a schematic representation of an optical observation device according to the invention.

DETAILED DESCRIPTION OF THE INVENTION

An optical observation device 100 will serve for observing an eye 22 and will be used in ophthalmic surgery. It is suitable for the alternating observation of the anterior eye segment and the retina.

Optical observation device 100 has two basic components, a microscope means 1 and a visualizing means 2. Microscope means 1 advantageously involves an operating microscope, which is known in and of itself, for observing the anterior segment of eye 22. A visual operating microscope 1 is shown in this example of embodiment. Optionally, it may also be designed as a digital operating microscope. In comparison to operating microscope 1, visualizing means 2 represents an attachment module, which can be introduced into the beam path of operating microscope 1.

Operating microscope 1 is disposed on a retaining device 14 by means of a positioning device 11. Retaining device 14 may involve a suspension system, by means of which the operating microscope is attached to a ceiling 15 of a room. Alternatively, retaining device 14 may also involve a floor stand or a component of a floor stand. Positioning device 11 for operating microscope 1 is advantageously designed in such a way that it permits a maximum of 6 degrees of freedom x, y, z, r, theta, phi.

Operating microscope 1 has a principal objective 3 through which pass two stereoscopic observation beam paths. Provided in each observation beam path is a magnification means 4, for example, in the form of a zoom system or a Galileo changing system, a beam splitter for coupling a beam path of a data reflection, as well as a tube optics 8. In addition, operating microscope 1 provides two eyepieces 9.

Visualizing means 2 is attached to operating microscope 1 by means of a retaining device 13. Retaining device 13 advantageously involves a suspension system for visualizing means 2 on operating microscope 1.

In the following, optical observation device 100 comprises the visual stereoscopic operating microscope 1 for the anterior eye segment and a digital stereoscopic visualizing system 2 for the retina—for example, a digital retina microscope, whereby the digital visualizing system 2 can be swung in and out alternately into the observation beam path of operating microscope 1 by means of a suitable holding means 10, 12, 13, so that stereoscopic images can be produced alternately of the anterior and posterior eye segments. For this purpose, visualizing means 2 is attached to the operating microscope by means of retaining device 13, advantageously via a rotating joint or hinge 10, whereby rotating joint or hinge 10 is designed for swinging visualizing means 2 in and out of the beam path of operating microscope 1.

Visualizing means 2 is disposed on retaining device 13 via a positioning device 12. Positioning device 12 for visualizing means 2 is advantageously designed in such a way that it permits a maximum of 6 degrees of freedom x, y, z, r, theta, phi.

Visualizing means 2 will be designed for the generation of stereoscopic images of the retina of eye 22. For this purpose, visualizing means 2 first provides at least one digital camera 21 for recording digital images of the retina of eye 22. For example, it may be provided that a shutter is provided in the beam path in front of camera 21, which produces two parts of the beam path that alternate sequentially, one after the other, over time, so that a stereo image is produced.

In another configuration, which is shown in the figure, visualizing means 2 is designed as a type of small intrinsic or unique microscope. Visualizing means 2 provides a first optical element 17, which produces an intermediate image of the retina, and a second optical element 18, which corresponds to a principal objective of an operating microscope. First optical element 17 in this case is advantageously designed in such a way that it produces an intermediate image of the retina between optical elements 17 and 18. In addition, a magnification means 19, e.g., a zoom system, and a tube optics 20 can be provided in each of the beam paths of visualizing means 2. In addition, visualizing means 2 has an illumination device 23.

Finally, optical observation device 100 also provides a control device 16, which particularly involves a type of monitoring or control means. Control device 16 particularly serves for exchanging data between visualizing means 2 and operating microscope 1, which is characterized by data connections 24 and 25. In particular, data in the form of image data/video data and data for adjusting the working modes of "anterior eye" and "retina" are exchanged between visualizing means 2 and operating microscope 1 by means of control device 16.

Image data of the retina, which are recorded by camera 21, are transmitted via data connection 24 to control device 16 and from there via data connection 25 to a display 7 of data reflection in operating microscope 1. In addition, operating microscope 1 provides an optical element 6, which couples display 7 of the data reflection to the imaging beam path of operating microscope 1, whereby this is produced by means of beam splitter 5 for coupling the beam path of the data reflection.

Optical observation device 100, which is shown in the figure, makes possible the alternate stereoscopic imaging of the anterior eye and the retina. The basic concept involves the use of a conventional operating microscope 1 for the anterior eye segment. A visualizing means 2, for example, a so-called retina digiscope, is used instead of the ophthalmoscopic loupe/reducing lens combination. The stereoscopic images of the retina that are produced with the visualizing means 2 can be reflected with the help of the data reflection into eyepiece 9 of operating microscope 1. The entire visualizing system can thus be used in the two working modes, "anterior eye" and "retina".

The images recorded with camera 21 of visualizing means 2 are displayed on a suitable stereoscopic display 7 in operating microscope 1. If operating microscope 1 is a visual system, the stereoscopic image data of visualizing means 2 can be reflected by means of data reflection into eyepiece 9 of operating microscope 1.

Visualizing means 2 is shown in the figure with a first optics 17 for the generation of an intermediate image of the retina. This optics group 17 may also be removed. In this case, a direct contact glass and the rest of the optical elements 18, 19, 20 of visualizing means 2 are used.

The positioning of visualizing means 2 at a short distance from the eye advantageously leads to a compact optics for the observation beam path. For this reason, it is possible to guide the illumination 23 of the retina between the two observation beam paths and thus to avoid reflections.

The variable magnification, which can be provided with optical element 19, can be used for the purpose of varying the object field on the retina. The use of different ophthalmoscopic loupes or contact glasses can thus be dispensed with.

Optical element 18 can be designed either as an element with fixed focal length or as a varioscope and can be used for focusing.

Visualizing means 2 can be automatically aligned in the lateral direction by evaluating the camera signals—for example, centering on the pupil of eye 22—and by controlling positioning device 12. The imaging optics of visualizing means 2 can be automatically focused onto the fundus either by moving the entire visualizing means 2 by means of positioning device 12 or by focusing with the help of optical elements 17 and 18. A tracking of eye 22 in the three axes x, y and z and a corresponding followup can be conducted with the help of positioning device 12 and/or by focusing with the help of optical elements 17 and 18.

Visualizing means 2 can be swung in and out, so that the position and thus the focus of operating microscope 1 remains in place on anterior eye 22. Thus both systems—operating microscope 1 and visualizing means 2—always remain focused on the respective objects, the anterior and posterior regions of the eye, when these systems are swung in and out.

Control device 16 transmits the video data between visualizing means 2 and operating microscope 1. It also controls the settings for the two working modes of "anterior eye" and "retina", that is, an activation of the autofocus for systems 1 and 2, a positioning of systems 1 and 2, or the switching on and off of the illumination for systems 1 and 2 as needed or not needed. In the "retina" working mode, operating microscope 1 can assume the function of a surrounding field observation: Thus, for example, what is found in the surrounding region of eye 22 can be monitored and displayed, for example, the orientation of instruments.

LIST OF REFERENCE SYMBOLS

1 Microscope means for observing the anterior eye segment
2 Means for visualizing
3 Principal objective
4 Magnification means (zoom system or Galileo changing system)
5 Beam splitter for coupling the beam path of the data reflection
6 Optical element, which couples the display of the data reflection to the observation beam path of the microscope means.
7 Display of the data reflection
8 Tube optics
9 Eyepiece
10 Rotating joint or hinge for swinging the visualizing means in and out of the observation beam path of the microscope means
11 Positioning device for the microscope means
12 Positioning device for the visualizing means
13 Retaining device for attaching the visualizing means to the microscope means
14 Retaining device for the microscope means
15 Ceiling
16 Control device
17 Optical element of the visualizing means, which produces an intermediate image of the retina
18 Optical element, which corresponds to a principal objective of a microscope
19 Magnification means (zoom system)
20 Tube optics
21 Camera (digital camera)
22 Eye
23 Illumination means
24 Data connection
25 Data connection
100 Optical observation device for observing an eye

The invention claimed is:
1. An optical observation device for observing an eye, having a microscope means for observation of the anterior segment of the eye, and having a means for visualizing the retina of the eye, with at least one camera by which images of the retina are recorded, is hereby characterized in that the microscope means comprises an objective, in that the visualizing means, as seen from the direction of the eye to be observed, is designed as an attachment module in front of the objective of the microscope means, in that the at least one camera of the visualizing means is disposed on a positioning device and can be selectively positioned in front of the objective of the microscope means by means of the positioning device, and in that the optical observation device has a display for displaying the images produced by the camera and/or that the microscope means has at least one eyepiece and that the optical observation device has a means for reflecting the images produced by the camera into the at least one eyepiece.

2. The optical observation device according to claim 1, further characterized in that the microscope means has at least one observation beam path and that the visualizing means is disposed in the observation beam path so that it can be alternately swung in and out by means of the positioning device.

3. The optical observation device according to claim 1 or 2, further characterized in that the visualizing means has at least one first optical element for generating an intermediate image of the retina.

4. The optical observation device according to claim 3, further characterized in that the camera is disposed in the plane of the intermediate image, which is produced by the first optical element.

5. The optical observation device according to claim 1, further characterized in that the visualizing means has a means for producing a stereo image.

6. The optical observation device according to claim 1, further characterized in that the visualizing means has at least one other second optical element.

7. The optical observation device according to claim 1, further characterized in that a protective covering is provided for the visualizing means.

8. The optical observation device according to claim 1, further characterized in that the visualizing means has an illumination means for illuminating the eye.

9. The optical observation device according to claim 1, further characterized in that it has a control device, particularly for controlling the visualizing means and/or the positioning device of the visualizing means and/or the microscope means.

10. The optical observation device according to claim 6, wherein the at least one other second optical element comprises at least one of an objective element and an optical magnification means.

11. The optical observation device according to claim 4, wherein the first optical element is provided in such a way that it produces an intermediate image of the retina between the first optical element and at least one other second optical element.

12. The optical observation device according to claim 3, characterized in that the intermediate image of the retina is provided within the visualizing means.

* * * * *